United States Patent
Klickstein et al.

(10) Patent No.: US 11,179,364 B2
(45) Date of Patent: Nov. 23, 2021

(54) LICOFLIGOZIN FOR THE TREATMENT OF NON-ALCOHOLIC STEATOHEPATITIS

(71) Applicant: NOVARTIS AG, Basel (CH)

(72) Inventors: Lloyd Klickstein, Newton, MA (US);
C. Daniel Meyers, Littleton, MA (US);
Chinweike Ukomadu, Chestnut Hill, MA (US)

(73) Assignee: Novartis AG, Basel (CH)

( * ) Notice: Subject to any disclaimer, the term of this patent is extended or adjusted under 35 U.S.C. 154(b) by 34 days.

(21) Appl. No.: 16/624,527

(22) PCT Filed: Jun. 20, 2018

(86) PCT No.: PCT/IB2018/054554
§ 371 (c)(1),
(2) Date: Dec. 19, 2019

(87) PCT Pub. No.: WO2018/235020
PCT Pub. Date: Dec. 27, 2018

(65) Prior Publication Data
US 2021/0145794 A1    May 20, 2021

Related U.S. Application Data

(60) Provisional application No. 62/522,735, filed on Jun. 21, 2017.

(51) Int. Cl.
*A61K 31/70* (2006.01)
*A61K 31/357* (2006.01)
*A61P 1/16* (2006.01)
*A61K 31/7048* (2006.01)

(52) U.S. Cl.
CPC ........ *A61K 31/357* (2013.01); *A61K 31/7048* (2013.01); *A61P 1/16* (2018.01)

(58) Field of Classification Search
CPC .................................................. A61K 31/7048
USPC .......................................................... 514/23
See application file for complete search history.

(56) References Cited

U.S. PATENT DOCUMENTS 8,466,114 B2 *   6/2013   Bebernitz ................ C07H 7/04
514/23

FOREIGN PATENT DOCUMENTS

WO         2011/048112 A1    4/2011

OTHER PUBLICATIONS

Novartis Pharmaceuticals Effect of LIK066 on Body weight in patients with elevated body mass index Clinical Trial NCT02470403, clinicaltrials.gov/ct2/show/NCT02470403, 2015 (Year: 2015).*

(Continued)

*Primary Examiner* — Shengjun Wang
(74) *Attorney, Agent, or Firm* — Emily T. Wu

(57) ABSTRACT

The disclosure concerns the use of LIK066 in the treatment, prevention or delay of non-alcoholic steatohepatitis.

8 Claims, 4 Drawing Sheets

(56) References Cited

OTHER PUBLICATIONS

Novartis Pharmaceuticals "Effect of LIK066 on glucose absorption in patients with type 2 diabetes mellitus," Clinical Trial NCT01915849, clinicaltrials.gov/ct2/show/results/NCT01915849, 2013, (Year: 2013).*
Cabelleria et al. "Nonalcoholic steatohepatitis and diabetes," Endocrinol Nutr. 2016, vol. 63, No. 8, pp. 377-379 (Year: 2016).*
Yasushi Honda et al., "The Selective SGLT2 Inhibitor Ipragliflozin Has a Therapeutic Effect on Nonalcoholic Steatohepatitis in Mice", PLOS One. Jan. 5, 2016; vol. 11, No. 1, p. e0146337, XP055508894.
U.S. Appl. No. 62/522,735.

* cited by examiner

STUDY DESIGN:

| 28 days (-44 to -16 days) | 14 days (-15 to -1 days) | 12 weeks (1 to 84 days) | 28 days (85-112 days) |
|---|---|---|---|
| Screen | Baseline | Treatment | Recovery and follow up |
| | | LIK066 150 mg Po QD (n=44) | |
| | | LIK066 30 mg Po QD (n=44) | |
| | | Placebo Po QD (n=22) | |

FIG. 1

Assessment Schedule

| Epoch | SCREENING | Baseline | Treatment | | | | | | | | | EOS[2] |
|---|---|---|---|---|---|---|---|---|---|---|---|---|
| Visit Name | Screening | Baseline | Treatment | | | | | | | | | EOS |
| Visit Numbers[1] | 1 | 101 | 201[3] | 202[3] | 203[3] | 204[3] | 205[3] | | | | 207[3] | 399 |
| Days | -44 to -16 | -15 to -1 | 1 | 7 | 14 | 28 | 42 | | | 56 | 84 | 112 |
| Time (post-dose) | - | - | 0h | - | - | - | 0h | 0h[3] | 1h | 2h | 0h | - |
| Informed consent[4] | X | | | | | | | | | | | |
| Pharmacogenetic Informed Consent[5] | X | | | | | | | | | | | |
| Inclusion / Exclusion criteria | X | X | | | | | | | | | | |
| Medical history/current medical conditions | X | | | | | | | | | | | |
| Demography | X | | | | | | | | | | | |
| Alcohol Test and Drug Screen | X | X | | | | | | | | | | |
| Hepatitis and HIV Screen | X | | | | | | | | | | | |
| Pregnancy and assessments of fertility[6] | X | | X | | | X | | X | | | X | X |
| Physical Examination | X | X | | X | X | X | X | X | | | X | X |
| Body Temperature | X | X | X | X | X | X | X | X | | | X | X |
| Body Height | X | | | | | | | | | | | |
| Body Weight | X | X | X | X | X | X | X | X | | | X | X |
| Waist circumference | X | X | X | X | X | X | X | | | | X | X |
| BMI | X | X | X | X | X | X | X | X | | | X | X |
| waist hip ratio | X | X | X | | | | | | | | | |
| Blood Pressure and Pulse Rate[7] | X | X[8] | X | X | X | X[8] | X | X[8] | | | X[8] | X |
| ECG evaluation | X | X | X | X | X | X | X | | | | X | X |
| Blood chemistry | X | X | X | X | X | X | X | X | | | X | X |

FIG. 2

Assessment Schedule

| Epoch | SCREENING | Baseline | Treatment | | | | | | | | | | EOS[2] |
|---|---|---|---|---|---|---|---|---|---|---|---|---|---|
| Visit Name[1] | Screening | Baseline | | | | | Treatment | | | | | | EOS |
| Visit Numbers[1] | 1 | 101 | 201[3] | 202[3] | 203[3] | 204[3] | 205[3] | | 206 | | | 207[3] | 399 |
| Days | -44 to -10 | -15 to -1 | 1 | 7 | 14 | 28 | 42 | | 56 | | | 84 | 112 |
| Time (post-dose) | - | - | 0h | - | - | - | 0h | 6h[9] | 1h | 2h | 4h | 6h | 0h | - |
| HbA1C | X | | X | | | | | | | | | X | |
| Hematology | X | X | X | X | X | X | X | | | | | X | X |
| Urinalysis | X | X | X | X | X | X | X | | | | | X | X |
| Fasting lipid panel[4] | X | X | X | | | | X | | | | | X | X |
| Coagulation Panel[10] | X | X | | | | | | | | | | | |
| Fasting insulin and glucose[5] | | | X | | | | | X | | | | X | X |
| HOMA-IR | | | X | | | | | | | | | X | X |
| Biomarker blood collection[12] | | | X | | | | X | | | | | X | |
| Pharmacogenetic sample collection[5] | | | X | | | | | | | | | | |
| PK blood collection | | | | X | X | X | X | X | X | X | X | X | |
| Stool Collection[13] | | | X | | | | | | | | | X | |
| Randomization | | | X | | | | | | | | | | |
| Dose administration | | | | | | | | X[14] | | | | | |
| Fibroscan[15] | | X | | | | | | X[16] | | | | X | |
| MRI[16] | | X | | | | | | | | | | X | X[17] |
| Comments | | | | | | | | As required | | | | | |
| Concomitant therapies | | | | | | | | As required | | | | | |
| Study completion information | | | | | | | | | | | | | X |
| Adverse Events | | | | | | | | As required | | | | | |
| Serious Adverse Events | | | | | | | | As required | | | | | |

FIG. 3

[1] Visit structure given for internal programming purpose only.

[2] If a patient withdraws from the study, or if study medication is discontinued for any reason, the patient should be scheduled for a subsequent visit at which time all assessments at the EOS visit should be performed.

[3] All assessments to be performed pre-dose.

[4] Informed consent must be provided by all patients before any screening procedures are performed. The pharmacogenetic assessment is optional and requires a separate informed consent to be signed.

[5] Pharmacogenetic samples are scheduled at V201 (0 h), however consent may be provided by the patient at any time during the study and samples may be collected at subsequent visit. A separate optional consent is required.

[6] Serum pregnancy tests are performed at Screening and end of study; urine tests may be used at other timepoints.

[7] Blood pressure and pulse rate is measured in a sitting position unless otherwise noted.

[8] Measured in sitting and standing positions to assess orthostatic hypotension.

[9] Fasting lipid panel includes total cholesterol, LDL, HDL and Triglycerides. Direct LDL is measured pre-dose at V201, V205, V207, and EOS.

[10] Coagulation panel includes PT/INR and aPTT.

[11] Assessed PRIOR to drug administration.

[12] Assessment includes (but are not limited to): circulating microRNAs, inflammatory and liver fibrosis markers (IL-8, hsCRP, IL1b, TNFα and ELF), CK18M30, OWL fiber test, collagen neoepitopes and OW Liver test.

[13] Optional

[14] Patients are provided with a supply of study medication to self-administer once daily for 12 weeks (Day 2 to Day 84). Study medication is administered by site personnel on all visit days. Patients should bring all used and unused medications, and diaries, to each visit.

15 Optional assessment; also referred to as "Liver ultrasonographic elastography". Fibroscan is the preferred method to measure liver stiffness. If Fibroscan is unavailable, alternative technology to assess liver stiffness is considered upon consultation with the sponsor.

[16] MRI of abdomen and liver in all subjects. Quantification of liver fat is performed on all subjects; Analysis of abdominal fat MRI based endpoints is performed only in subset of subjects and where available.

[17] Assessment is only to be performed at EOS if a patient withdraws from the study, or discontinues study treatment early for any reason.

[18] A thorough review of any concomitant medications (including medication name, dose, unit, frequency, and route) is performed at every visit.

FIG. 4

LICOFLIGOZIN FOR THE TREATMENT OF NON-ALCOHOLIC STEATOHEPATITIS

RELATED APPLICATIONS

This application is a 371 U.S. national phase application of international application number PCT/IB2018/054554, filed 20 Jun. 2018, which claims the benefit of U.S. provisional application Ser. No. 62/522,735 filed 21 Jun. 2017; each of which is incorporated by reference herein in its entirety.

FIELD OF THE DISCLOSURE

The present disclosure relates to pharmaceutical uses of LIK066, their pharmaceutically acceptable salts, and prodrugs thereof specifically for the treatment of non-alcoholic steatohepatitis ("NASH").

BACKGROUND OF THE DISCLOSURE

Obesity has become a major global health problem that contributes causally to and exacerbates many serious co-morbidities including hypertension, dyslipidemia, type 2 diabetes (T2DM) and importantly non-alcoholic fatty liver disease (NAFLD). While there are as yet no medications approved for treatment of NAFLD, numerous medicines are available to treat other obesity-related diseases. Interestingly, relatively few agents that are effective, safe or scalable to the size of the affected population are available for the treatment of obesity itself). A novel mechanism to lower body weight is via inhibition of the sodium glucose co-transporters 1 and 2 (SGLTs) resulting in inhibition of the glucose absorption in the gut and reabsorption in the kidney).

The presence of obesity and insulin resistance, often with clinical features of the metabolic syndrome, leads to a high-risk profile for the development of NAFLD. NAFLD is one of the most common liver diseases worldwide with a global prevalence estimated at 25%. Estimates of obesity among patients diagnosed with NAFLD by imaging show that more than 50% are obese albeit with regional variations; 64% for Asians, 37% for Europeans and 57% for North Americans. NAFLD encompasses a broad spectrum of disease severity, ranging from isolated steatosis to its more severe form with variable degrees of hepatocyte inflammation, necrosis and liver fibrosis, known as nonalcoholic steatohepatitis (NASH), which can progress to cirrhosis and end stage liver disease. In support of the link between obesity and fatty liver linked hepatic injury, weight loss either through bariatric surgery, diet or exercise leads to improvement in histologic NASH. This suggests that targeting obesity in NASH patients is likely to limit or reverse liver disease progression.

Therefore, there is a need to provide treatments for NASH in a subject in need of such treatment that can address the different aspects of this complex condition, in any patient in need of such treatment while demonstrating an acceptable safety and/or tolerability profile. The inhibition of both SGLT1 and SGLT2 might provide additional benefits for improving treatment efficacy and response rates.

SUMMARY OF THE DISCLOSURE

LIK066 is a dual SGLT1/2 inhibitor which is being developed as a novel treatment for obesity. Single and multiple doses of LIK066 induced glucosuria in healthy volunteers (HVs) and patients with T2DM, and significantly lowered glucose area under the time-concentration curve (AUC) after an oral glucose tolerance test (OGTT) in patients with T2DM. LIK066 was found to be safe and tolerated, had a favorable pharmacokinetic profile, and resulted in up to 3% placebo-adjusted weight loss over just 2 weeks in both healthy subjects and patients with T2DM. LIK066 at 150 mg daily dose (as qd, b.i.d or tid) results in a significant weight loss in obese patients (~6%) after 12 week treatment. Furthermore, twelve week treatment with LIK066 at 150 mg qd in normoglycemic and dysglycemic subjects was generally safe and well tolerated with diarrhea observed as a dose-limiting toxicity.

LIK066 is a potent inhibitor of SGLT2 and SGLT1 and has a high selectivity against other glucose transporters (GLUTs). LIK066 had no significant inhibitory hERG activity at the maximal soluble concentration (16 μM). The tissue distribution study in rats indicated relatively low distribution to the central nervous system and reproductive organs. In rats, [$^{14}$C] LIK066-related radioactivity was excreted in both urine and feces, mainly as metabolites.

LIK066 is a substrate for P-glycoprotein (P-gp), but its good permeability and solubility characteristics are expected to limit the contribution of efflux transporters towards its intestinal absorption. LIK066 exhibits good solubility and permeability properties. Direct glucuronidation (via the UDP-glucuronosyl transferase (UGT1A9)) was found to be the predominant clearance pathway of LIK066 in human hepatocytes, followed by oxidative metabolism (CYP3A4). In vitro studies indicated that LIK066 has low potential to act as a perpetrator of pharmacokinetic drug interactions. The pharmacokinetics of LIK066 was noted to be comparable between the tablet and solution formulations following administration of a single dose of 50 mg/dog in a crossover design to dogs.

The principal target organs of toxicity identified in oral studies in rats (up to 26-weeks in duration) and dogs (up to 13-weeks in duration) were the gastrointestinal tract, kidney, urinary tract, bone, liver and adrenal glands; effects in these systems were considered related, if indirectly, to inhibition of SGLT1/2. In both species, reduced body weight gain was observed at almost all doses and body weight loss occurred at the highest doses evaluated. Rats tolerated LIK066 at doses up to 100 mg/kg for 4 weeks, with reversible weight loss and 1 death at the high dose; doses up to 30 mg/kg were tolerated for 26 weeks. Dogs did not tolerate doses ≥10 mg/kg for prolonged periods (i.e., ≥6 weeks) due to body weight loss, fecal changes and dehydration. The no observed adverse effect level (NOAEL) for LIK066 was 5 mg/kg/day in the rat and 0.5 mg/kg/day in the dog.

In accordance with a first aspect of the present disclosure, there is provided a method for the treatment or prevention of non-alcoholic steatohepatitis (NASH) in a subject in need of such treatment, which comprises administering to said subject a therapeutically effective amount of an a inhibitor of SGLT1 and SGLT2, e.g., LIK066, or a pharmaceutically acceptable salt thereof.

In another aspect, the present disclosure relates to the compound LIK066, or a pharmaceutically acceptable salt or prodrug thereof, for use in the treatment or prevention of NASH.

In yet another embodiment, the present disclosure relates to a pharmaceutical composition comprising LIK066, or a pharmaceutically acceptable salt or prodrug thereof, for use in the treatment or prevention of NASH.

In another embodiment, the present disclosure relates to the use of LIK066, or a pharmaceutically acceptable salt or prodrug thereof, in the manufacture of a medicament for use in the treatment or prevention of NASH.

In accordance with another aspect of the present disclosure, there is provided a method for the treatment or prevention of NASH in a subject with Type 2 diabetes and/or obesity, which comprises administering to said subject a therapeutically effective amount of LIK066, or a pharmaceutically acceptable salt thereof.

In another aspect, the present disclosure relates to the compound LIK066, or a pharmaceutically acceptable salt or prodrug thereof, for use in the treatment or prevention of NASH in a patient with Type 2 diabetes and/or obesity.

In yet another embodiment, the present disclosure relates to a pharmaceutical composition comprising LIK066, or a pharmaceutically acceptable salt or prodrug thereof, for use in the treatment or prevention of NASH in a patient with Type 2 diabetes and/or obesity.

In another embodiment, the present disclosure relates to the use of LIK066, or a pharmaceutically acceptable salt or prodrug thereof, in the manufacture of a medicament for use in the treatment or prevention of NASH in a patient with Type 2 diabetes and/or obesity.

BRIEF DESCRIPTION OF THE DRAWINGS

FIG. 1 depicts the study design.
FIG. 2 depicts the assessment schedule.
FIG. 3 depicts the assessment schedule.
FIG. 4 depicts the assessment schedule.

DETAILED DESCRIPTION OF THE DISCLOSURE

In a first embodiment, the present disclosure relates to a method for the treatment or prevention of NASH, which comprises administering to said subject a therapeutically effective amount of LIK066, or a pharmaceutically acceptable salt thereof.

In a second embodiment, the present disclosure relates to the method according to the first embodiment, wherein about 25-500 mg of LIK066 is administered.

In a third embodiment, the present disclosure relates to the method according to any one of the first or second embodiments, wherein LIK066 is administered once per day.

In a fourth embodiment, the present disclosure relates to the method according to any one of the previous embodiments, wherein about 30 mg of LIK066 is administered.

In a fifth embodiment, the present disclosure relates to the method according to any one of the previous embodiments, wherein about 150 mg of LIK066 is administered.

In a sixth embodiment, the present disclosure relates to the method according to any one of the first through fifth embodiments, wherein the subject is obese, defined as an individual having a Body Mass Index (BMI) $\geq 23$ kg/m$^2$.

In a seventh embodiment, the present disclosure relates to the compound LIK066, or a pharmaceutically acceptable salt or prodrug thereof, for use in the treatment or prevention of NASH.

In an eighth embodiment, the present disclosure relates to a pharmaceutical composition comprising LIK066, or a pharmaceutically acceptable salt or prodrug thereof, for use in the treatment or prevention of NASH.

In a ninth embodiment, the present disclosure relates to the pharmaceutical composition according to the eighth embodiment, wherein the composition comprises 25-500 mg of LIK066.

In a tenth embodiment, the present disclosure relates to the pharmaceutical composition according to the eighth or ninth embodiment, wherein the composition comprises about 30 mg of LIK066.

In an eleventh embodiment, the present disclosure relates to the pharmaceutical composition according to the eighth or ninth embodiment, wherein the composition comprises about 150 mg of LIK066.

In a twelfth embodiment, the present disclosure relates to the pharmaceutical composition according to any one of the eighth through eleventh embodiments, wherein the pharmaceutical composition is administered once per day.

In a thirteenth embodiment, the present disclosure relates to the pharmaceutical composition according to any one of the eighth through twelfth embodiments, wherein the subject has a BMI$\geq 23$ kg/m$^2$.

In a fourteenth embodiment, the present disclosure relates to the use of LIK066, or a pharmaceutically acceptable salt or prodrug thereof, in the manufacture of a medicament for use in the treatment or prevention of NASH.

In a fifteenth embodiment, the present disclosure relates to the pharmaceutical composition according to the fourteenth embodiment, wherein the medicament comprises 25-500 mg of LIK066.

In a sixteenth embodiment, the present disclosure relates to the pharmaceutical composition according to the fourteenth or fifteenth embodiment, wherein the composition comprises about 30 mg of LIK066.

In a seventeenth embodiment, the present disclosure relates to the pharmaceutical composition according to the fourteenth or fifteenth embodiment, wherein the composition comprises about 150 mg of LIK066.

In an eighteenth embodiment, the present disclosure relates to LIK066 for use in the treatment of NASH.

In a nineteenth embodiment, the present disclosure relates to LIK066 for use in the treatment of NASH in a subject with Type 2 Diabetes Mellitus.

In a twentieth embodiment, the present disclosure relates to LIK066 for use in the treatment of PCOS in a subject with a BMI$\geq 23$ kg/m$^2$.

In a twenty-first embodiment, the present disclosure relates to a pharmaceutical unit dose comprising 30 mg of LIK066.

In a twenty-second embodiment, the present disclosure relates to a pharmaceutical unit dose comprising 150 mg of LIK066.

The details of the disclosure are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

Unless specifically stated, as used herein, the term "about" refers to a range of values ±10% of a specified value. For example, the phrase "about 200" includes ±10% of 200, or from 180 to 220.

A "pharmaceutically acceptable salt" is intended to mean a salt of a free base/free acid of a compound represented by formula (I) or a compound of the present disclosure (e.g., LIK066) that is not toxic, biologically intolerable, or otherwise biologically undesirable. Preferred pharmaceutically acceptable salts are those that are pharmacologically effective and suitable for contact with the tissues of patients without undue toxicity, irritation, or allergic response. Such salts are known in the field (e.g., S. M. Berge, et al, "Pharmaceutical Salts", J. Pharm. Sci., 1977, 66:1-19; and "Handbook of Pharmaceutical Salts, Properties, Selection, and Use", Stahl, R. H., Wermuth, C. G., Eds.; Wiley-VCH and VHCA: Zurich, 2002).

LIK066 is an inhibitor of the sodium-glucose co-transporter-1 (SGLT1) and sodium-glucose co-transporter-2 (SGLT2). LIK066 has the following chemical structure:

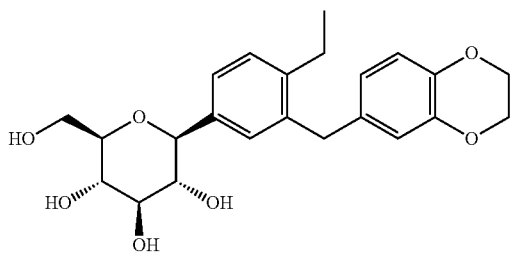 [SMILES: CCc1ccc([C@@H]2O[C@H](CO)[C@@H](O)[C@H](O)[C@H]2O)cc1Cc1ccc2c(c1)OCCO2]

LIK066 has the following IUPAC name: (2S,3R,4R,5S,6R)-2-(3-((2,3-dihydrobenzo[b][1,4]dioxin-6-yl)methyl)-4-ethylphenyl)-6-(hydroxymethyl)tetrahydro-2H-pyran-3,4,5-triol.

LIK066 for use in the present disclosure is either obtained in the free form, as a salt thereof, a co-crystal, or as prodrug derivatives thereof.

Furthermore, LIK066 including its salts, can also be obtained in the form of its hydrates, or include other solvents used for its crystallization. LIK066 may inherently or by design form solvates with pharmaceutically acceptable solvents (including water); therefore, it is intended that the disclosure embrace both solvated and unsolvated forms. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like.

The term "hydrate" refers to the complex where the solvent molecule is water. LIK066, including salts, hydrates and solvates thereof, may inherently or by design form polymorphs.

The higher oral bioavailability of LIK066 may give rise to the following beneficial effects relating to less bioavailable compounds: (i) an enhanced biological effect may be achieved after oral administration; (ii) an earlier onset of action may be observed following oral administration; (iii) a lower dose may be needed to achieve the same effect; (iv) a higher effect may be achieved by the same dose or (v) a prolonged action may be observed at the same dose.

The term "subject" as used herein typically refers to a human, especially to a human patient diagnosed with NASH.

The term "treatment" as used herein refers to any type of treatment that imparts a benefit to a subject affected with NASH.

For the above-mentioned indications (the conditions and disorders) the appropriate dosage will vary depending upon, for example, the host, the mode of administration and the nature and severity of the condition being treated. However, in general, satisfactory results in are indicated to be obtained at a daily dosage of from about 0.01 mg to about 100 mg/kg body weight, preferably from about 1 mg to about 30 mg/kg body weight, e.g., 10 mg/kg. An indicated daily dosage is in the range from about 0.1 mg to about 1000 mg, preferably from about 25 mg to about 500 mg, conveniently administered, for example, in an oral dose delivered 1-3 times per day. In one embodiment, about 30 mg of LIK066 is administered once a day. In another embodiment, about 150 mg of LIK066 is administered once per day.

For use according to the disclosure, LIK066 may be administered in any usual manner, e.g., orally, for example in the form of tablets, capsules or drinking solutions; rectally, for example in the form of suppositories; intravenously, for example in the form of injection solutions or suspensions; or transdermal, for example in the form of a patch.

In one embodiment, the manner of administration is oral administration, for example in the form of a tablet, capsule or drinking solution. In one embodiment, the manner of administration is rectal administration, for example in the form of a suppository. In one embodiment, the manner of administration is transdermal administration, for example in the form of a patch. In one preferred embodiment, the manner of administration is oral administration.

Preferred pharmaceutical compositions comprise LIK066 in association with at least one pharmaceutical carrier or diluent. Such compositions may be manufactured in conventional manner. Unit dosage forms may contain LIK066 in an amount greater than or equal to 2.5 mg, for example greater than or equal to 10 mg, such as for example greater than or equal to 25 mg. Unit dosage forms may also contain LIK066 in an amount of greater than or equal to 2.5 mg, 10 mg, 40 mg, 50 mg, 75 mg, or 100 mg or greater than or equal to 150 mg or 200 mg.

Unit dosage forms may contain LIK066 in an amount less than or equal to 100 mg, for example less than or equal to 100 mg, such as for example less than or equal to 50 mg or for example less than or equal to 10 mg or for example less than or equal to 2.5 mg. Unit dosage forms may also contain LIK066 in an amount in the range including, but not limited to, from 1-100 mg, e.g., 1-75 mg or 1-60 mg, such as 2-55 mg.

The pharmaceutical compositions according to the disclosure are compositions for enteral administration, such as oral or rectal administration; or parenteral administration, such as intramuscular, intravenous, and nasal or transdermal administration, to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the disclosure may be, for example, in unit dose form, such as in the form of ampoules, vials, suppositories, dragées, tablets or capsules. Compositions for transdermal administration are described in Remington's Pharmaceutical Sciences 16$^{th}$ Edition Mack; Sucker, Fuchs and Spieser, Pharmazeutische Technologie, 1$^{st}$ Edition, Springer.

Example of NASH Treatment Via a Randomized, Placebo Controlled Study

The following abbreviations and terms will be used throughout the following example, which is in reference to a clinical trial study.

LIST OF ABBREVIATIONS

AE adverse event
ALP alkaline phosphatase
ALT alanine aminotransferase
ANCOVA analysis of covariance
AST aspartate aminotransferase
b.i.d twice a day
BMI Body Mass Index
BUN blood urea nitrogen
CFR U.S. Code of Federal Regulation
CPK creatine kinase
CRF Case Report/Record Form (paper or electronic)
CRO Contract Research Organization
CTC Common Toxicity Criteria
CV coefficient of variation
DBP Diastolic Blood Pressure
DMC Data Monitoring Committee
ECG Electrocardiogram
EDC Electronic Data Capture
FDA Food and Drug Administration
GCP Good Clinical Practice
GGT Gamma-glutamyl transferase
h hour
HBV Hepatitis B virus
HCV Hepatitis C virus
HIV human immunodeficiency virus
hsCRP high-sensitivity c reactive protein
ICF Informed Consent Form
ICH International Conference on Harmonization of Technical Requirements for Registration of Pharmaceuticals for Human Use
IEC Independent Ethics Committee
IL1b Interleukin 1 beta
INR International Normalized Ratio
IRB Institutional Review Board
IRT Interactive Response Technology
LDH lactate dehydrogenase
LFT Liver function test
LLOQ lower limit of quantification
MedDRA Medical dictionary for regulatory activities
mg milligram(s)
ml milliliter(s)
MRI Magnetic Resonance Imaging
NAFLD Non-alcoholic fatty liver disease
NASH Non-alcoholic steatohepatitis
p.o. oral
PD pharmacodynamic(s)
PDFF Proton Density Fat Fraction
PK pharmacokinetic(s)
qd once a day
RBC red blood cell(s)
SAE serious adverse event
SBP Systolic Blood Pressure
sCR serum creatinine
SD standard deviation
SGLT Sodium glucose co-transporter
SOM Site Operations Manual
SUSAR Suspected Unexpected Serious Adverse Reactions
t.i.d thrice a day
T2DM Type 2 Diabetes Mellitus
TBL total bilirubin
TNFalpha Tumor Necrosis Factor alpha
ULN upper limit of normal
WBC white blood cell(s)
WHO World Health Organization
WoC Withdrawal of Consent Terms Assessment A procedure used to generate data required by the study
Cohort A specific group of subjects fulfilling certain criteria
Control drug Any drug(s) (an active drug or an inactive drug, such as a placebo) which is used as a comparator to the investigational drug being tested in the trial
Dosage Dose of the study treatment given to the subject in a time unit (e.g., 100 mg once a day, 75 mg twice a day)
Electronic data capture (EDC) is the electronic acquisition of clinical study data using data collection systems, such as Web-based applications, interactive voice response systems and clinical laboratory interfaces.
Electronic Data Capture (EDC) EDC includes the use of Electronic Case Report Forms (eCRFs) which are used to capture data transcribed from paper source forms used at the point of care.
Enrollment Point/time of subject entry into the study at which informed consent must be obtained (i.e., prior to starting any of the procedures described in the protocol)
Epoch Interval of time in the planned conduct of a study. An epoch is associated with a purpose (i.e., screening, randomization, treatment, follow-up) which applies across all arms of a study.
Investigational drug The study drug whose properties are being tested in the study; this definition is consistent with U.S. C.F.R. § 21 Section 312.3 and Directive 2001/20/EC and is synonymous with "investigational new drug," "Investigational Medicinal Product," or "test substance"
Randomization number A unique identifier assigned to each randomized subject, corresponding to a specific treatment arm assignment
Screen Failure A subject who is screened but is not treated or randomized
Source Data/Document Source data refers to the initial record, document, or primary location from where data comes. The data source can be a database, a dataset, a spreadsheet or even hard-coded data, such as paper or eSource
Study treatment Any drug or combination of drugs administered to the study participants as part of the required study procedures; includes investigational drug(s), control(s) or background therapy Study treatment discontinuation When the subject permanently stops taking study treatment prior to the defined study treatment completion date Subject A trial participant (can be a healthy volunteer or a patient)

Subject number A unique number assigned to each subject upon signing the informed consent. This number is the definitive, unique identifier for the subject and should be used to identify the subject throughout the study for all data collected, sample labels, etc.

Variable A measured value or assessed response that is determined in specific assessments and used in data analysis to evaluate the drug being tested in the study Withdrawal of consent (WoC) Withdrawal of consent from the study is defined as when a subject does not want to participate in the study any longer, and does not want any further visits or assessments, and does not want any further study related contact, and does not allow analysis of already obtained biologic material Pharmacokinetic Definitions and Symbols AUClast The area under the plasma (or serum or blood) concentration-time curve from time zero to the time of the last quantifiable concentration [mass×time/volume]

Cmax The observed maximum plasma (or serum or blood) concentration following drug administration [mass/volume]

Tmax The time to reach the maximum concentration after drug administration [time]

Study Design

Primary Objective

| Primary objective(s) | Endpoints related to primary objective(s) |
|---|---|
| To determine the effect of LIK066 on Liver Function Test after 12 weeks of treatment | Circulating alanine aminotransferase (ALT) levels |

Secondary Objectives

| Secondary objective(s) | Endpoints related to secondary |
|---|---|
| To determine the effect of LIK066 on intrahepatic lipid after 12 weeks of treatment. | Percent (%) Liver fat as measured by Magnetic Resonance Imaging (MRI-PDFF) |
| To determine the effect of LIK066 on total body weight after 12 weeks of treatment | Percent change in total body weight |
| To determine the effect of LIK066 on non-invasive markers of liver fibrosis after 12 weeks of treatment | Enhanced liver fibrosis panel (ELF: PIIINP, TIMP-1, and Hyaluronic acid) |
| To determine the safety and tolerability of LIK066 | Adverse events, safety laboratory tests including basic chemistry profile and liver biochemical tests |
| To evaluate the pharmacokinetics (PK) of LIK066 in NASH patients | Cmax, Tmax, AUClast |
| To determine the effect of LIK066 on aspartate aminotransferase (AST) after 12 weeks of treatment | Circulating aspartate aminotransferase (AST) levels |

Study Design

This is anon-confirmatory, multicenter, patient and investigator blinded, randomized, placebo-controlled, parallel group study in patients with NASH. The sponsor is unblinded to the treatment assignment of all patients to allow for continuous unblinded safety monitoring. The study consists of a 28 day screening period (Day −44 to Day −16), a baseline period of 14 days (Day −15 to Day −1), a treatment period of 12 weeks (Day 1 to Day 84), and a study completion evaluation approximately 28 days after the last drug administration. The patients are advised to maintain their recommended diet during the study. The study design scheme is shown below:

TABLE 1

Study Design

| 28 days (−44 to −16 days) Screen | 14 days (−15 to −1 days) Baseline | 12 weeks (1 to 84 days) Treatment | 28 days (85-112 days) Recovery and follow up |
|---|---|---|---|
| | | LIK066 150 mg Po QD (n = 44) *LIK066 30 mg Po QD (n = 44) Placebo Po QD (n = 22) | |

Patients are required to fast overnight for at least 8 hours before each clinic visit for blood collection and at least 3-4 hours before MRI procedure where applicable. Patients who meet the inclusion/exclusion criteria at screening present to the study site for baseline assessments, including determination of the percent liver fat content and optional assessment of exploratory imaging endpoints (subcutaneous and visceral fat content and local hepatic inflammation) by MRI (Day −15 to Day −1). All baseline safety evaluation results must be available prior to the first dosing. At the beginning of the study after eligibility has been confirmed, patients are randomized in a 2:1 ratio to receive either LIK066 at 150 mg qd OR matching placebo qd, by oral administration. A third, 30 mg qd arm is initiated after 33 patients have been enrolled in the initial two arm portion of the study. For the entire study, patients are randomized to either LIK066 at 150 mg qd, 30 mg qd or matching placebo at a ratio of 2:2:1. The placebo group is supplemented by an equal number of historic controls from trials via an informative prior trial using a Bayesian analysis. As reflected in the inclusion criteria, Asians tend to have NASH at much lower BMI. Therefore, patients with Asian race are stratified by BMI of <30 kg/m² or ≥30 kg/m² at baseline, all other patients are stratified by BMI of <35 kg/m² or ≥35 kg/m² at baseline. The Asian race is based on the patient self-report captured on the demography eCRF. Finally, patients identifying themselves as Pacific Islanders are grouped with the non-Asian group.

The first dose of study medication is administered to patients under study site personnel supervision prior to launch on Day 1. Patients are provided with a supply of study medication and allowed to leave the site to continue the study as outpatients. Patient compliance track pill counts at each visit, patient diaries and PK sampling as indicated in the assessment table outlined in FIGS. 2-4. Patients continue to take study medication once daily for twelve weeks (day 2 to day 84), as instructed by the investigator. Patients return to the clinical site once weekly for the first 2 weeks (days 7 and 14) and then return to the clinical site every 2 weeks (days 28, 42 and 56). On day 56, the patients take the study medication at the site prior to breakfast, following which pharmacokinetic sampling occurs for up to 6 hours post dose. Patients return to the clinic on day 84 for study assessments including MRI evaluation at the end of treatment. Finally, there is an end of study (EOS) evaluation visit approximately 28 days after the last drug administration. Safety assessments include physical examinations, ECGs, vital signs, standard clinical laboratory evaluations (hematology, blood chemistry, urinalysis,) adverse event and serious adverse event monitoring. Details of safety, PK, and PD assessments can be found in FIGS. 2-4.

Rationale for Study Design

This randomized, multi-center, patient and investigator blinded, placebo-controlled study is designed to assess the efficacy of LIK066 relative to placebo in patients with NASH. The completed study enrolls 110 patients who are randomized in a 2:2:1 ratio to 150 mg daily, 30 mg daily and placebo. However, at the beginning of the study, patients are enrolled into only two arms: 150 mg daily dose and placebo, randomized at 2:1. An interim analysis is performed once approximately 27 of the first 33 patients have completed week 12 visit and the data becomes available. This approach allows the early evaluation of the impact of 150 mg dose where significant weight loss, a variable in NASH improvement is expected. If the interim analysis does not suggest efficacy (<20% chance of a positive outcome when the study is eventually completed) the study is terminated. To ensure maintenance of the a priori defined 2:2:1 ratio, the 30 mg dose arm can be activated by sponsor as early as when 33 patients have enrolled into the study (22 of the 150 mg dose arm and 11 placebos), resulting in a change of randomization to 2:4:1 (150 mg:30 mg:placebo) for the remaining 77 subjects and maintenance of the completed study ratio at 2:2:1. This randomization scheme for the overall study allows for the reduction in the number of placebo patients by using historic control patients from previous trials in comparable patient population.

In order to maintain the scientific integrity of the study, the investigators and patients remain blinded to their treatment allocation. To allow close monitoring of biochemical safety parameters which overlap with the primary efficacy outcome (ALT) and performance of exploratory biomarkers the Novartis Clinical Trial Team (CTT) are unblinded throughout the study.

To ensure that no bias is introduced by imbalance of severity of disease across different arms of the study, patients are stratified to active or placebo arms on the basis of BMI. Currently there is no approved pharmacotherapy for patients with NASH. All patients are encouraged to adhere to local advice regarding diet and exercise regimens. To keep the dietary intake as constant as possible during the study, patients participating in this study are advised to adhere to American Heart Association (AHA) diet or equivalent if there is a country specific recommended diet.

Rationale for Dose/Regimen, Route of Administration and Duration of Treatment

The primary efficacy endpoint for dose/exposure-response analysis for LIK066, from previously completed clinical studies, was body weight loss, and other pharmacodynamic endpoints such as urinary and plasma glucose. The estimated ED50 and ED90 of LIK066 based on once a day dosing were approximately 5 mg and 50 mg, respectively, based on a body weight loss model. The estimated ED50 and ED90 based on other relevant pharmacodynamics endpoints such as urinary and plasma glucose were approximately 3-10 mg and 30-100 mg, respectively. The 150 mg dose is considered because it is in the ≥ED90 range and has been shown in a previous phase 2 study to lead to significant weight loss. Therefore this dose is tested first, with introduction of the 30 mg dose later to assure futility evaluation prior to enrollment of the entire cohort for the study. Of note, in the 12 week study in obese patients, the 150 mg daily dose was generally safe and well tolerated. The primary AE was diarrhea, which did not lead to any discontinuation of treatment or patient withdrawals from the study. The diarrhea associated with LIK066 could be mitigated by dietary modification such as reduction in carbohydrate intake. Body weight loss is an important factor in therapeutic development for NASH as weight loss through either bariatric surgery or life style modification deters progression of the disease.

The pharmacokinetic elimination half-life of LIK066 ranged from 10-16 hours, which, in combination with the glucose urinary excretion data at the proposed doses is supportive of once daily dosing. Furthermore, exposure of LIK066 in non-cirrhotic NASH patients (patient population in this study) is in the range of that observed in previous studies since these patients are not expected to have hepatic dysfunction.

The duration of the study is based on findings in published literature relating to Obeticholic acid and elafibranor, which demonstrate that 12 weeks provides an ample time frame to test biochemical changes likely to result from improvement to the NASH phenotype. In addition observations from other studies with surgical, diet and pharmacotherapy suggest that 12 weeks is also an adequate timeframe to test an effect on liver fat.

Rationale for Choice of Comparator

A placebo is used as a comparator to provide estimates of net drug effects for efficacy and safety/tolerability assessments.

Population

The study population is comprised of male and female adult overweight or obese patients with EITHER histologic evidence of NASH on liver biopsy within 2 years prior to randomization and elevated ALT OR phenotypic diagnosis of NASH based on elevated ALT, Type 2 diabetes mellitus by elevated HbA1c and increased BMI; full details are below. Approximately 110 patients are randomized in the study. At least 88 subjects are expected to complete the study.

Inclusion Criteria

Patients with a phenotype consistent with NASH eligible for inclusion in this study must fulfill all of the following criteria:

1. Written informed consent must be obtained before any assessment is performed.

2. Presence of NASH as demonstrated by ONE of the following:

EITHER

Histologic confirmed NASH based on liver biopsy obtained 2 years or less before randomization with a fibrosis level of F1, F2 or F3, in the absence of a histological diagnosis of alternative chronic liver diseases AND ALT≥50 IU/L (males) or ≥35 IU/L (females) at screening;
OR
Phenotypic diagnosis of NASH based on presence of ALL THREE of the following at screening:
  ALT≥50 IU/L (males) or ≥35 IU/L (females) AND;
  BMI≥27 kg/m$^2$ (in patients with a self-identified race other than Asian) or ≥23 kg/m$^2$ (in patients with a self-identified Asian race) AND;
  Diagnosis of Type 2 diabetes mellitus by HbA1C: ≥6.5% and ≤10%
3. Patients must weigh no more than 150 kg (330 lbs.) to participate in the study. Inclusion of subjects with higher weights up to 200 kg (440 lbs.) may occur if a MRI scanner with a table weight of 200 kg (440 lbs.) is available.
4. Male and female patients 18 years or older (at the time of the screening visit).
5. Able to communicate well with the investigator, to understand and comply with the requirements of the study.

Exclusion Criteria

Patients with a phenotype consistent with NASH fulfilling any of the following criteria are not eligible for inclusion in this study:
 1. History or presence of other concomitant liver diseases including:
    Hepatitis B or C virus (HCV, HBV) infection. Patients with history of HCV who attained sustained virologic response more than 3 years prior to screening are not excluded.
    Primary biliary cholangitis (PBC)
    Primary sclerosing cholangitis (PSC)
    Alcoholic liver disease
    Definite autoimmune liver disease or overlap hepatitis
    Suspected or confirmed Gilbert's syndrome
    Known bile duct obstruction
    Suspected or proven hepatocellular cancer
 2. History or current diagnosis of ECG abnormalities indicating significant risk of safety for patients participating in the study such as:
    Concomitant clinically significant cardiac arrhythmias, e.g., sustained ventricular tachycardia, and clinically significant second or third degree AV block without a pacemaker
    History of familial long QT syndrome or known family history of Torsades de Pointes in a first degree relative.
 3. Use of GLP-1 agonists such as liraglutide, exenatide, lixisenatide, albiglutide or dulaglutide; SGLT-2 inhibitors such as canagliflozin, empagliflozin or dapagliflozin; Thiazolidinediones (TZDs) such as pioglitazone; FXR agonists such as obeticholic acid (OCA) and any pharmacologically active weight-loss medications such as lorcaserin prior to 6 weeks of screening visit and up to end of study visit.
 4. Known positivity for Human Immunodeficiency Virus (HIV) infection.
 5. eGFR≤45 ml/min/1.73 m$^2$ based on MDRD equation
 6. Patients with contraindications to MRI imaging, including:
    Brain aneurysm clip
    Implanted neural stimulator
    Implanted cardiac pacemaker or defibrillator, or presence of intracardiac wires
    Prosthetic heart valves
    Cochlear implant
    Ocular foreign bodies that might be ferromagnetic (e.g., metal shavings)
    Other implanted medical devices (e.g., insulin pumps)
    Metal shrapnel or bullets still in the body
    Severe claustrophobia
    Tattoos (as determined by the Investigator and Imager)
    Weight in excess of MRI machine capacity
    Joint replacements
 7. Inability to reliably quantify alcohol consumption based upon local study physician judgment.
 8. Current or history of significant alcohol consumption for a period of more than 3 consecutive months within 1 year prior to screening (significant alcohol consumption is defined as more than 20 g/day in females and more than 30 g/day in males, on average) and/or a score on the AUDIT questionnaire ≥8 as administered by the site as part of the medical history.
 9. History of treated or untreated malignancy of any organ system, other than localized basal cell carcinoma of the skin or treated cervical intraepithelial neoplasia, within the past 5 years, regardless of whether there is evidence of local recurrence or metastases.
 10. Clinical evidence of hepatic decompensation or severe liver impairment as defined by the presence of any of the following abnormalities:
    Serum albumin<32 g/L
    INR>1.3
    Direct bilirubin>13 mg/L
    ALT or AST>8×ULN
    Alkaline Phosphatase>3×ULN
    History of esophageal varices, ascites or hepatic encephalopathy
    Splenomegaly
 11. Platelet count<120×109/L.
 12. Presence of cirrhosis on liver biopsy or clinical diagnosis of cirrhosis.
 13. Type I diabetes and uncontrolled diabetes defined as HbA1c>10% within 60 days prior to screening.
 14. Prior or planned (during the study period) bariatric surgery (e.g., gastroplasty, roux-en-Y gastric bypass).
 15. Patients on treatment with the following medicines unless they are on a constant dose for ≥3 months before screening: anti-diabetic medications, insulin (if ≥25% change in dose), beta-blockers, thiazide diuretics, fibrates, statins, niacin, ezetimibe, vitamin E (if doses >400 IU/day; doses >800 IU/day are prohibited), thyroid hormone, psychotropic medications, estrogen or estrogen containing birth control.
 16. Patients taking medications prohibited by the protocol. These medications include the following:
    GLP-1 agonists such as liraglutide, exenatide, lixisenatide, albiglutide or dulaglutide
    SGLT2 inhibitors such as empagliflozin, canagliflozin, dapagliflozin OR ertugliflozin
    Pharmacologically active weight-loss medications (eg. lorcaserin, phentermine/topiramate, bupropion-naltrexone HCL, orlistat)
    Treatment with drugs that alter intestinal motility (e.g., erythromycin, metoclopramide, tegaserod, methylnaltrexone, alvimopan, loperamide, diphenoxylate and atropine (Lomotil) and difenoxin and atropine (Motofen))
    Treatment with drugs that have a high incidence of diarrhea (e.g., Orlistat, Acarbose).
    Chronic systemic steroid treatment or systemic steroids for >7 consecutive days for worsening of an underlying condition.
    Treatment with or use of strong inhibitors of CYP3A4/5 including boceprevir, clarithromycin, conivaptan, grapefruit juice, indinavir, itraconazole, ketoconazole, lopinavir, fazodone, nelfinavir, posaconazole, ritonavir, saquinavir, telaprevir, telithromycin, and voriconazole.

Strong CYP3A inducers including avasimibe, carbamazepine, phenytoin, rifampin, St. John's wort.

General UGT inhibitors including probenecid and valproic acid.

17. For those patients that have had a previous liver biopsy: Significant weight loss (>15%) or change in clinical status (in the opinion of the investigator) since the diagnostic liver biopsy to screening.
18. Chronic use (i.e., >3 months immediately prior to baseline visit) of high dose Nonsteroidal Anti-inflammatory Drugs (NSAIDS) as evaluated by investigator.
19. History of non-adherence to medical regimens, or patients who are considered by the investigator to be unable to comply reliably with the requirements of the study.
20. Donation or loss of 400 ml or more of blood within eight (8) weeks prior to initial dosing, or longer if required by local regulation.
21. History of inflammatory bowel disease.
22. History of non-alcohol drug abuse within the 12 months prior to dosing, or evidence of such abuse as indicated by the laboratory assays conducted during screening and baseline.
23. Women of child-bearing potential, defined as all women physiologically capable of becoming pregnant, unless they are using basic methods of contraception during dosing and for 5 days (approximately 5 times the terminal half-life) after stopping study medication. Basic contraception methods include:

Total abstinence (when this is in line with the preferred and usual lifestyle of the subject. Periodic abstinence (e.g., calendar, ovulation, symptothermal, post-ovulation methods) and withdrawal are not acceptable methods of contraception Female sterilization (have had surgical bilateral oophorectomy with or without hysterectomy) or tubal ligation at least six weeks before taking study treatment. In case of oophorectomy alone, only when the reproductive status of the woman has been confirmed by follow up hormone level assessment Male sterilization (at least 6 months prior to screening). For female subjects on the study the vasectomized male partner should be the sole partner for that subject Barrier methods of contraception: Condom or Occlusive cap.

Use of oral (estrogen and progesterone), injected or implanted combined hormonal methods of contraception or placement of an intrauterine device (IUD) or intrauterine system (IUS), or other forms of hormonal contraception that have comparable efficacy (failure rate <1%), for example hormone vaginal ring or transdermal hormone contraception. In case of use of oral contraception women should have been stable on the same pill for a minimum of 3 months before taking study treatment.

Women are considered post-menopausal and not of child bearing potential if they have had 12 months of natural (spontaneous) amenorrhea with an appropriate clinical profile (e.g., age appropriate, history of vasomotor symptoms) or have had surgical bilateral oophorectomy (with or without hysterectomy), total hysterectomy or tubal ligation at least six weeks ago. In the case of oophorectomy alone, only when the reproductive status of the woman has been confirmed by follow up hormone level assessment is she considered not of child bearing potential.

24. Pregnant or nursing (lactating) women, where pregnancy is defined as the state of a female after conception and until the termination of gestation, confirmed by a positive hCG laboratory test.
25. History of hypersensitivity to study drug or to drugs of similar chemical classes.
26. Use of other investigational drugs within 5 half-lives of screening, or within 30 days whichever is longer; or longer if required by local regulations.
27. History of liver transplantation or current placement on a liver transplant list.
28. Symptomatic genital or urinary tract infection in the 4 weeks prior to first study visit
29. Subjects who experienced ketoacidosis, lactic acidosis, or hyperosmolar coma within 6 months of Screening Visit, or between Screening Visit and Baseline Day −1.

30. Treatment with or use of inhibitors of CYP3A4/5 including boceprevir, clarithromycin, conivaptan, grapefruit juice (not a treatment but rather an use), indinavir, itraconazole, ketoconazole, lopinavir, fazodone, nelfinavir, posaconazole, ritonavir, saquinavir, telaprevir, telithromycin, and voriconazole up to 7 days prior to the start of study treatment until the end of study. Strong CYP3A inducers including avasimibe, carbamazepine, phenytoin, rifampin, St. John's wort up to 7 days prior to start of study treatment until the end of study. General UGT inhibitors including probenecid, valproic acid up to 7 days prior to start of study treatment until the end of study.

Treatment Arms

Initially patients are assigned to one of the following two treatments (A or B) in a ratio of 2:1. Study treatments are defined as:

A: LIK066 150 mg

B: Matching placebo

An additional treatment arm is introduced after 33 patients have been enrolled into the initial 150 mg and matching placebo arms. When the additional dosing arm is included, patients are assigned to one of the following three treatments (C, D or E) in a ratio of 2:4:1.

C: LIK066 150 mg

D: LIK066 30 mg

E: Matching placebo

Treatment Assignment and Randomization

Randomized treatment is assigned to individual patients by way of a randomization number. Randomization numbers are assigned in ascending, sequential order to eligible patients via an IRT system.

The randomization number is only used to identify which treatment the patient has been randomized to receive. The Patient number assigned to a patient at screening remains the unique identifier for the patient throughout the study.

The randomization numbers are generated using the following procedure to ensure that treatment assignment is unbiased and concealed from subjects and investigator staff. A subject randomization list is produced by the IRT provider using a validated system that automates the random assignment of subject numbers to randomization numbers. These randomization numbers are linked to the different treatment arms, which in turn are linked to medication numbers. A separate medication list is produced by or under the responsibility of Novartis Drug Supply Management using a validated system that automates the random assignment of medication numbers to packs containing the investigational drug. Randomization is stratified by BMI at baseline (<30 kg/m² or ≥30 kg/m² for patients with an Asian race, or <35 kg/m² or ≥35 kg/m² for all other patients). The race is based on the race the patient self-reports as captured on the demography eCRF.

Treatment Blinding

This is a patient and investigator-blinded study. Patients and investigators remain blinded to study treatment throughout the study, except where indicated below. Drug product is supplied as a double blinded patient packs and the identity of the treatments is concealed by the use of study drugs that are all identical in packaging, labeling, schedule of administration, appearance, and odor.

Site Staff

With the exception of any unblinded site staff identified below, all site staff (including study investigator and study nurse) are blinded to study treatment throughout the study. Unblinding a single subject at site for safety reasons (necessary for subject management) occurs via an emergency system in place at the site.

Sponsor Staff

The sponsor remains unblinded to the treatment assignment of all patients to allow for continuous unblinded safety monitoring throughout the study. Sponsor clinical staff are required to assist in the management and re-supply of investigational drug product. These individuals are not provided with randomization lists directly but may be unblinded through communication of drug re-supply needs via the IRT system.

The clinical trial team is allowed to share unblinded results with other sponsor staff (e.g., decision boards) as required for internal decision making on the study or the project while the study is ongoing.

Dispensing the Study Drug

LIK066 is administered to the subject via the oral route. Patients are provided with a supply of study medication to self-administer once daily for 12 weeks (Day 2 to Day 84) before lunch. Study medication is administered by site personnel on all visit days.

Sponsor qualified medical personnel are readily available to advise on trial related medical questions or problems.

Emergency Breaking of Assigned Treatment Code

Emergency code breaks are only undertaken when it is required to in order to treat the patient safely. Most often, study treatment discontinuation and knowledge of the possible treatment assignments are sufficient to treat a study patient who presents with an emergency condition. Emergency treatment code breaks are performed using the IRT. When the investigator contacts the system to break a treatment code for a patient, he/she must provide the requested patient identifying information and confirm the necessity to break the treatment code for the patient. The investigator then receives receive details of the investigational drug treatment for the specified patient and communication confirming this information. The system automatically informs the Novartis monitor for the site and the Study Team that the code has been broken.

It is the investigator's responsibility to ensure that there is a dependable procedure in place to allow access to the IRT system at any time in case of emergency. The investigator provides the protocol number, the study drug name (if available) and the patient number.

In addition, oral and written information to the patient is provided on how to contact the investigator's backup in cases of emergency, or when the investigator is unavailable, to ensure that un-blinding can be performed at any time.

Patients whose treatment has been unmasked must be discontinued from study treatment.

Study Completion and Post-Study Treatment

A patient is considered to have completed the study when the patient has completed the last planned visit (see FIGS. 2-4). The study as a whole is considered completed when all randomized subjects have completed the last visit planned in the protocol or have discontinued the study prematurely. The investigator must provide follow-up medical care for all subjects who are prematurely withdrawn from the study, or must refer them for appropriate ongoing care.

Visit Schedule and Assessments

FIGS. 2-4 list all of the study visits and assessments and indicates with an "X" when the assessments are performed. Patients are seen for all visits on the designated day, or as close to it as possible. Missed or rescheduled visits should not lead to automatic discontinuation. Patients who prematurely discontinue the study for any reason are scheduled for a visit as soon as possible, at which time all of the assessments listed for the final visit are performed. At this final visit, all dispensed investigational product is reconciled and the adverse event and concomitant medications reconciled on the eCRF. Patients are contacted for safety evaluations during the 30 days following the last administration of study treatment.

Patient Demographics/Other BL Characteristics

Pertinent demographic and baseline characteristic data is collected on all patients. Relevant medical history/current medical conditions data is also collected until signature of informed consent. Investigators have the discretion to record abnormal test findings on the medical history CRF, if in their judgment, the test abnormality occurred prior to the informed consent signature.

Treatment Exposure and Compliance

Compliance is assessed by the investigator and/or study personnel at each visit using pill counts and information provided by the patient. This information is captured in the source documents at each visit. All study treatment dispensed and returned is recorded in the Drug Accountability Log. The site is also required to complete the appropriate Dosage Administration Record eCRF to record any study drug regimen changes or interruptions.

Efficacy Pharmacodynamic (PD) samples are collected at the timepoints defined in the Assessment schedule as set forth in FIGS. 2-4. PD samples are obtained and evaluated in all subjects, including the placebo group. Pharmacodynamic assessments include:

Liver function tests (ALT and AST)
Proton Density Liver Fat Fraction (PDFF) by Magnetic Resonance Imaging (MRI)
Anthropometric assessments (Height, Body Weight, BMI and waist:hip ratio)
Markers of liver fibrosis
Fasting lipids
Other assessments include the following:
Body Weight
  Body weight (to the nearest 0.1 kilogram [kg] on a calibrated scale. The measurement is performed with the study subject in underwear and without shoes), as indicated in the Assessment Schedule. Voiding before weight measurement is required. Details of these assessments are provided in the site operations manual.
  Body mass index (BMI) is calculated as (Body weight (kg)/[Height (m)]2)
Body Height: Height is measured at screening visit and is used to calculate BMI.

Fasting lipid panel: Blood samples are collected for a fasting lipid panel, including total cholesterol, HDL-cholesterol and LDL-cholesterol, triglycerides, free glycerol and free fatty acids as per FIGS. 2-4. Lipid measurements are collected under fasted conditions. Detailed information is provided in the central laboratory manual.

MRI: Patients undergo magnetic resonance imaging twice during the course of the study (Baseline and End of Treatment) to quantitate liver fat, and assess exploratory MRI endpoints as outlined FIGS. 2-4). End of Treatment assessment is not performed if the patient prematurely discontinues treatment prior to Week 8.

Liver function tests: ALT, AST, GGT, ALP (total), total bilirubin, and albumin are assessed as indicated in FIGS. 2-4. The effect on circulating ALT levels is the primary efficacy variable for this study. If the total bilirubin concentration is increased above 1.5 times the upper limit of normal, direct and indirect reactive bilirubin is quantified. ALP isoenzymes and 5'NT are also measured but do not form part of the screening requirements or safety data set.

Markers of Liver Fibrosis
  Fibroscan® (Optional): is performed to assess liver stiffness (in kPa)
  Enhanced liver fibrosis Test (ELF) panel: the following are assessed: hyaluronic acid (HA), tissue inhibitor of metalloproteinases (TIMP-1), and amino-terminal pro-peptide of procollagen type III (PIIINP).
  Additional fibrosis markers are assessed, including but not limited to collagen neo-epitopes (such as ProC3), FIB4, APRI and NAFLD scores Waist circumference and waist:hip ratio: Waist circumference is measured to the nearest 0.1 cm at visits indicated in FIGS. 2-4.

Blood chemistry: Albumin, alkaline phosphatase, total bilirubin, bicarbonate/$CO_2$, calcium, cholesterol, chloride, creatinine, CRP, γGT, glucose, LDH, CPK, inorganic phosphorus, lipase, amylase, magnesium, potassium, total protein, AST, ALT, sodium, triglycerides, urea/BUN and uric acid. If the total bilirubin concentration is increased above 1.5 times the upper limit of normal, direct and indirect reacting bilirubin should be differentiated.

Blood Pressure and Pulse Rate:
  Blood pressure (BP)
  Systolic blood pressure (SBP)
  Diastolic blood pressure (DBP)
  Pulse Hematology: Hemoglobin, hematocrit, red blood cell count, white blood cell count with differential (e.g., neutrophils, basophils, eosinophils, monocytes, lymphocytes), erythrocyte sedimentation rate, and platelet count are measured. Coagulation parameters including aPTT, PT and INR are also assessed; methods for assessment and recording are as known in the art.

Urinalysis: Urine test by dipstick: Leukocytes, Nitrite, pH, Specific gravity, Protein, Glucose, Ketones, Urobilinogen, Bilirubin, Blood/hemoglobin. If the dipstick result is positive for protein, nitrite, leucocytes and/or blood, the sample is sent for microscopic analysis of WBC, RBC and casts.

ECG evaluation: PR interval, QRS duration, heart rate, RR, QT, QTc. The Fridericia QT correction formula (QTcF) is used for clinical decisions.

Pharmacokinetics

PK samples are collected at the time points defined in the Assessment schedule as set forth in FIGS. 2-4. LIK066 concentration in plasma is determined by a validated liquid chromatography-tandem mass spectrometry (LC/MS/MS) method; the anticipated Lower Limit of Quantification (LLOQ) is 1.0 ng/mL. Concentrations below the LLOQ are reported as "zero" and used as such in summary statistics and pharmacokinetic analysis.

The following pharmacokinetic parameters are determined using the actual recorded sampling times and non-compartmental method(s) with Phoenix WinNonlin (Version 6.4 or higher): Cmax, Tmax, and AUClast from the plasma concentration-time data. Additional parameters may be determined as relevant.

Data Collection

Designated investigator staff enter the data required by the protocol into the Electronic Case Report Forms using fully validated software that conforms to 21 CFR Part 11 requirements. Designated investigator site staff are not given access to the EDC system until they have been trained. Validation checks for data discrepancies and, by generating appropriate error messages, allow the data to be confirmed or corrected before transfer of the data to Novartis or the CRO working on behalf of Novartis. The Investigator must certify that the data entered into the Electronic Case Report Forms are complete and accurate. After database lock, the investigator receives copies of the subject data for archiving at the investigational site.

Data not requiring a separate written record is defined in the Assessment schedule and is recorded directly on the CRFs. All other data captured for this study has an external originating source (either written or electronic) with the CRF not being considered as source. All data is recorded, handled and stored in a way that allows its accurate reporting, interpretation and verification.

Database Management and Quality Control

Novartis or designated CRO staff review the data entered into the CRFs by investigational staff for completeness and accuracy and instruct the site personnel to make any required corrections or additions. Queries are sent to the investigational site via the EDC system. Designated investigator site staff is required to respond to the query and confirm or correct the data. If the electronic query system is not used, a paper Data Query Form is faxed to the site. Site personnel complete and sign the faxed copy and fax it back to Novartis staff who make the correction to the database. The signed copy of the Data Query Form is kept at the investigator site. Concomitant medications entered into the database are coded using the WHO Drug Reference List, which employs the Anatomical Therapeutic Chemical classification system. Medical history/current medical conditions and adverse events are coded using the Medical dictionary for regulatory activities (MedDRA) terminology. Laboratory results are sent electronically to Novartis (or a designated CRO). The occurrence of relevant protocol deviations is determined. After these actions have been completed and the database has been declared to be complete and accurate, it is locked and made available for data analysis.

Data Analysis

The analysis is conducted on all subject data at the time the trial ends. Any data analysis carried out independently by the investigator is submitted to Novartis before publication or presentation.

Analysis Sets

For all analysis sets, patients are analyzed according to the study treatment received. The safety analysis set includes all patients who received any study drug. The PK analysis set includes all patients with at least one available valid (i.e., not flagged for exclusion) PK concentration measurement, who received any study drug and with no protocol deviations that impact on PK data. The PD analysis set includes all patients with available PD data and no protocol deviations with relevant impact on PD data.

Statistical Model, Hypothesis, and Method of Analysis

A Bayesian approach is used to analyze the change from baseline to Week 12 in ALT, which is assumed to follow a normal distribution with a known variance for both treatment arms. An informative prior worth approximately 17 patients (effective sample size set to equal to the planned sample size for the placebo arm) for the placebo treatment effect based on historical control data including but not limited to the FLINT trial and a non-informative prior for the LIK066 treatment effect is incorporated in the analysis. Median estimates, 90% credible intervals and posterior probabilities that the placebo-adjusted ALT reduction by LIK066 is (a) greater than 0 and (b) greater than 19 U/L (observed magnitude of net OCA drug effect in the FLINT trial) are provided for each active dosing arm as well as the combined active dosing arm if more than 1 dose is studied. For the combined active dosing arm estimates based on an informative prior worth approximately 52 patients (effective sample size set to equal to the planned sample size for the combined active dosing arm) for the placebo treatment effect are be provided.

A repeated measures analysis of covariance (ANCOVA) is performed for change from baseline ALT. The model includes effects for treatment, visit, treatment by visit interaction, stratification factor (BMI group), baseline, and baseline by visit interaction. The BMI group has the following 2 strata: 1) low BMI stratum (BMI<30 for Asians, BMI<35 for non-Asians) and 2) high BMI stratum (BMI>=30 for Asians, BMI>=35 for non-Asians). An unstructured variance-covariance structure is used to account for correlation among multiple measurements from the same patient and variance heterogeneity. If the unstructured covariance causes model convergence issues other simpler covariance structures are considered. Point estimates, the associated two-sided 90% confidence intervals as well as the p-values for treatment differences are obtained. The null hypothesis of no treatment difference vs placebo is tested at the one-sided 0.1 significance level for each active dosing arm and the combined active dosing arm if more than 1 dose is studied. Both untransformed and log-transformed ALT is analyzed, with log-transformed baseline in lieu of untransformed baseline as a covariate when log-transformed ALT is analyzed. For log-transformed ALT analysis the ratio to baseline results obtained by back transformation is reported.

Handling of Missing Values/Censoring/Discontinuations

Assuming missing at random, a patient with missing value at a visit still contributes to the estimation of the treatment effect at that particular visit as the likelihood-based repeated measures ANCOVA borrows information from non-missing values of this patient and other patients.

Sensitivity Analyses

As a sensitivity analysis the Bayesian analysis above is repeated with varying values of the effective sample size for the placebo prior. A further sensitivity analysis using different values of the common variance assumed in the likelihood function and the prior is performed as needed. A Bayesian analysis without assuming the variance is known in the likelihood function is performed as well.

If more than 10% of the data for the Bayesian analysis on the change from baseline to Week 12 in ALT are missing then as a sensitivity analysis the Last Observation Carried Forward (LOCF) approach and/or another method is used to impute missing data and the Bayesian analysis re-conducted.

Analysis of Secondary Variable(s)

The secondary PD variables of this study are:
  Intrahepatic lipid: Percent (%) Liver fat as measured by Magnetic Resonance Imaging (MRI).
  Anthropometric assessments: Weight, BMI, waist-to-hip (WTH) ratio
  AST: Change from baseline to week 12
  Non-invasive markers of liver fibrosis:
  Enhanced liver fibrosis panel (ELF) and fibrosis biomarker test (originally known as Fibrotest®/FibroSure®).

Baseline for all secondary parameters is defined as the last measurement prior to the first dose except for AST where baseline is the mean at baseline (V101) and pre-dose (V201) visits.

Log-transformed ratio to baseline % liver fat as well as change from baseline % liver fat, weight, BMI, and WTH ratio is analyzed. Parameters with more than one post-treatment measurement is subjected to the same repeated measures ANCOVA described for the primary analysis using log-transformed baseline in lieu of untransformed baseline as a covariate for the log-transformed data analysis. For parameters with only one post-treatment measurement an ANCOVA with treatment as a classification factor and baseline (or log-transformed baseline if applicable) as a covariate is employed.

ELF and fibrosis biomarker test data is analyzed similarly and the log-transformation applied prior to the analysis as needed. For % liver fat, if historical placebo control data in a similar patient population are identified in the literature or become available from in-house studies later on then they are incorporated into a Bayesian analysis as described for ALT.

Safety

Vital Signs

All vital signs data are listed by treatment group, subject, and visit/time and if ranges are available abnormalities (and relevant orthostatic changes) are flagged. Summary statistics are provided by treatment and visit/time.

ECG Evaluations

All ECG data is listed by treatment group, subject and visit/time, abnormalities are flagged. Summary statistics are provided by treatment and visit/time.

Clinical Laboratory Evaluations

All laboratory data is listed by treatment group, patient, and visit/time and if normal ranges are available abnormalities are flagged. Summary statistics are provided by treatment and visit/time. Selected lab markers such as AST, bilirubin, ALP, GGT, creatinine and BUN are analyzed using the repeated measures ANCOVA as described above.

Adverse Events

All information obtained on adverse events is displayed by treatment group and subject.

The number and percentage of subjects with adverse events is tabulated by body system and preferred term with a breakdown by treatment. A subject with multiple adverse events within a body system is only counted once towards the total of this body system.

Pharmacokinetics

LIK066 plasma concentrations are listed by treatment, patient, and visit/sampling time point. Descriptive summary statistics are provided by treatment and visit/sampling time point. Summary statistics include mean (arithmetic and geometric), SD, CV (arithmetic and geometric), median, minimum, maximum, and the frequency (n, %) of concentrations below the LLOQ. Concentrations below LLOQ are treated as zero in summary statistics and for PK parameter calculations. A geometric mean is not reported if the dataset includes zero values. Graphical methods are employed to show mean and individual concentration-time profiles.

Pharmacokinetic parameters are listed by treatment and patient and summarized by treatment with descriptive statistics as listed above. Since Tmax is generally evaluated by a nonparametric method, only median, minimum, and maximum are reported.

An exploratory assessment of dose proportionality for LIK066 is conducted if more than one LIK066 dose is studied. Log-transformed dose-normalized Day 56 AUC and Cmax is analyzed separately using an Analysis of Variance (ANOVA) with dose as the classification factor. The comparison between the 2 doses is made within the ANOVA framework. The ratio of geometric means and the associated 90% confidence interval (CI) for the 2 dose comparison is obtained by back-transforming the least squares mean treatment difference and the corresponding 90% C in the log domain to the original scale.

Pharmacokinetic/Pharmacodynamic Interactions

The relationship between Day 56 PK parameters (Cmax and AUC) and key PD parameters (including, but not limited to ALT and % liver fat) are explored using a graphical approach and descriptive statistics may be provided. Additional statistical analysis, such as ANOVA or regression, is performed, if necessary. Modelling approach is used to explore the PK/PD interactions.

Regulatory and Ethical Compliance

This clinical study is designed and implemented, executed and reported in accordance with the ICH Harmonized Tripartite Guidelines for Good Clinical Practice, with applicable local regulations (including European Directive 2001/20/EC, US CFR 21, and Japanese Ministry of Health, Labor, and Welfare), and with the ethical principles laid down in the Declaration of Helsinki.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method for the treatment of non-alcoholic steatohepatitis in a subject in need of such treatment, which comprises administering to said subject a therapeutically effective amount of LIK066, or a pharmaceutically acceptable salt or co-crystal thereof.

2. The method of claim 1, wherein 25-500 mg of LIK066 is administered.

3. The method of claim 2, wherein 30 mg of LIK066 is administered.

4. The method of claim 2, wherein 150 mg of LIK066 is administered.

5. The method according to claim 1, wherein LIK066 is administered once a day.

6. The method according to claim 1, wherein the subject has a body-mass index of greater than or equal to about 23 $kg/m^2$.

7. The method of claim 2, wherein 50 mg of LIK066 is administered.

8. A method for treating non-alcoholic steatohepatitis in a subject in need of such treatment, comprising administering to said subject 25-500 mg of LIK066, or co-crystal thereof.

* * * * *